(12) United States Patent
Rittenhouse et al.

(10) Patent No.: US 10,973,528 B2
(45) Date of Patent: Apr. 13, 2021

(54) MODULAR SYSTEM AND APPARATUS FOR TREATING WOUNDS

(71) Applicant: The Government of the United States of America, as represented by the Secretary of Homeland Security, Washington, DC (US)

(72) Inventors: Howard Rittenhouse, Washington, DC (US); Michael Bishop, Washington, DC (US); Michael Zeller, Washington, DC (US); Perry Jenkins, Washington, DC (US); Jonathan Yake, Washington, DC (US); Ronald Adrezin, East Lyme, CT (US); Michael Plumley, Washington, DC (US); Paola Jaramillo Cienfuegos, Stevensville, MD (US); Michael Daeffler, Washington, DC (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 16/838,362

(22) Filed: Apr. 2, 2020

(65) Prior Publication Data

US 2020/0375608 A1 Dec. 3, 2020

Related U.S. Application Data

(60) Provisional application No. 62/853,924, filed on May 29, 2019.

(51) Int. Cl.
*A61B 17/135* (2006.01)
*A61F 7/10* (2006.01)
(Continued)

(52) U.S. Cl.
CPC .............. *A61B 17/135* (2013.01); *A61F 7/10* (2013.01); *A61B 2017/00092* (2013.01);
(Continued)

(58) Field of Classification Search
CPC ........... A61B 2017/00199; A61B 2017/00544; A61B 2017/00092; A61B 2017/12004; A61B 17/135; A61B 17/132; A61F 7/10
See application file for complete search history.

(56) References Cited

U.S. PATENT DOCUMENTS 4,106,002 A * 8/1978 Hogue, Jr. ............. A61B 5/022
340/573.1
5,911,735 A * 6/1999 McEwen ............... A61B 5/1106
606/201

(Continued)

FOREIGN PATENT DOCUMENTS

| WO | 2012148472 A2 | 11/2012 |
| WO | 2014023960 A1 | 2/2014 |
| WO | 2015069360 A1 | 5/2015 |

*Primary Examiner* — Jocelin C Tanner
(74) *Attorney, Agent, or Firm* — Lavanya Ratnam; Kelly G. Hyndman (57) ABSTRACT

A modular wound treatment system includes a central modular hub having a modular connection for one or more pneumatically-actuated, modular components, such as a pneumatically-actuated soft robotic gripper component configured to curve and at least partially encircle the wound when actuated and thereby apply direct pressure to the wound, and a pneumatically-actuated tourniquet component configured to apply pressure proximal to the wound to limit the flow of arterial blood to the wound. The system also includes a pressurized gas supply in pneumatic communication with the modular connection, sensors for measuring the amount of pressure being applied by the pneumatically-actuated, modular components, a display for providing system information, and a controller for controlling the system.

(Continued)

Methods of treating a wounded subject using the system are also provided.

28 Claims, 6 Drawing Sheets

(51) Int. Cl.
    *A61B 17/12*     (2006.01)
    *A61B 17/00*     (2006.01)

(52) U.S. Cl.
    CPC ............ *A61B 2017/00199* (2013.01); *A61B 2017/00544* (2013.01); *A61B 2017/12004* (2013.01)

(56) References Cited

U.S. PATENT DOCUMENTS

| | | | |
|---|---|---|---|
| 6,746,470 B2 | 6/2004 | McEwen et al. | |
| 9,039,730 B1* | 5/2015 | McEwen | A61B 17/135 606/202 |
| 9,113,895 B2 | 8/2015 | McEwen et al. | |
| 9,931,126 B2 | 4/2018 | McEwen et al. | |
| 10,118,301 B2 | 11/2018 | Lessing et al. | |
| 10,136,900 B2 | 11/2018 | Menashe | |
| 2003/0139766 A1* | 7/2003 | McEwen | A61B 17/135 606/203 |
| 2004/0147956 A1* | 7/2004 | Hovanes | A61B 5/0225 606/202 |
| 2007/0191881 A1 | 8/2007 | Amisar et al. | |
| 2009/0124912 A1* | 5/2009 | McEwen | A61B 5/02255 600/495 |
| 2010/0204726 A1* | 8/2010 | McEwen | A61B 17/1355 606/202 |
| 2013/0218033 A1* | 8/2013 | Quinn | A61B 5/022 600/492 |
| 2015/0257968 A1 | 9/2015 | Vause et al. | |
| 2018/0272147 A1* | 9/2018 | Freeman | A61B 5/046 |

\* cited by examiner

MODULAR SYSTEM AND APPARATUS FOR TREATING WOUNDS

CROSS-REFERENCE TO RELATED APPLICATIONS

This application claims priority to U.S. Provisional Application 62/853,924, filed May 29, 2019, which is incorporated by reference in its entirety.

GOVERNMENT INTEREST

The subject matter of this disclosure was made with support from the United States Department of Homeland Security (101DHS). The Government of the United States of America has certain rights in this invention.

FIELD

This application describes a system that controls bleeding.

BACKGROUND

Unless stopped, blood loss from an injury can lead to death. A tourniquet around a bleeding arm or leg stops blood loss, but sometimes injures the limb. To minimize such injury, the tourniquet must evenly squeeze the limb at a pressure marginally high enough to stop blood flow.

Pneumatic tourniquet cuffs safely and effectively stop arterial blood flow. A pneumatic tourniquet cuff encircles a limb with an inflatable bladder. The inflated bladder expands and compresses the limb with an inward, radial force. The compression applied to the limb varies with the cuff inflation pressure.

Starving the limb of blood flow, also called arterial blood flow occlusion, leads to gangrene of the limb and other complications. Conventional techniques release the tourniquet pressure for five or ten minutes every two hours.

SUMMARY

A need exists for an apparatus and system for treating wounds that has a modular design, is adaptable to treat various sized wounds, can sense and report the applied pressure and time, and can provide signals and alarms to alert the operator of system functions and failures. A need also exists for an apparatus that is small enough to fit comfortably inside of a rescue helicopter, is portable enough to be carried by one able-bodied person and meets or exceeds the physical requirements for a deployable medical system. A need also exists for an apparatus that is highly resistant to corrosion and can operate in harsh environments, such as a battlefield.

The present disclosure describes a modular system intended for treatment of wounds to control bleeding and exsanguination of a wounded subject while providing feedback to the operator. The system, in an embodiment, utilizes pneumatically-controlled, pneumatically-actuated, modular components. These components can, for example, be a soft robotic gripper that applies direct pressure to the wound site, or a tourniquet that limits blood flow to the wound site. The system has a modular design; a central, modular, hub assembly interfaces with the various modular components. The system also includes a source of pressurized gas, a controller, and a modular component quick connection feature. This allows for a variety of modular attachments to be easily connected and fully integrated into the system within a matter of a few seconds. The central modular hub also actively regulates the amount of pressure applied by the components to the wounded subject, thus maintaining the proper level of pressure, and for an appropriate amount of time.

A modular design describes a situation where a product or system is organized into a number of assemblies or modules, each one adapted, for example, to complete a specific function. The modules interact with the hub and ultimately one another to carry out the system's present purpose. The modular design, according to an embodiment, identifies particular functions that achieve the overall product purpose, such as applying direct pressure, applying pressure proximal to a wound site, providing pneumatic controls, monitoring the system, and providing feedback. Modules that implement these individual operations are brought together to form the system, which can then perform its complete function.

When connected to the modular hub, the pneumatically controlled and actuated modular components are in signal communication with the modular hub, providing the modular hub with information and a system feedback loop. The modular hub includes a controller designed to govern the operation of the modular system. The modular system also includes pneumatic connections that supply gas to the modular components and the components then retain the gas when they are disconnected from the modular hub.

The modular system, according to an embodiment, is intended to be used by a basically trained field medic (user) on a patient (subject) suffering from severe lacerations or other grievous high-priority wounds such as lacerations and puncture wounds. The system has a practical application, for example, in battlefield operations, in that a field medic can quickly apply an appropriate modular component to a wounded subject, freeing the medic to continue to triage other wounded subjects.

According to various embodiments, the present modular system can be transported in a helicopter, and embodiments of the system meet or exceed Military Standard MIL-D-42048, which outlines military general requirements for deployable medical systems. Various embodiments of the modular system are held in a corrosion resistant, dustproof and moisture proof container that also protects the contents from vibration, shock and compression.

According to various embodiments, the present modular system for treating wounds includes a central modular hub having a modular connection for one or more or more pneumatically-actuated, modular components. The modular components include a pneumatically-actuated soft robotic gripper component containing a pneumatic network of channels and chambers, such as pneunets, the gripper component configured to curve and at least partially encircle the wound site when actuated and thereby apply direct pressure to the wound site. The modular components also include a pneumatically-actuated tourniquet component configured to apply pressure proximal to the wound site to limit the flow of blood to the wound site. The present system also includes a pressurized gas supply in pneumatic communication with the modular connection, one or more sensors for measuring the amount of pressure being applied by the one or more pneumatically-actuated, modular components, a controller for controlling the system, and a display for providing system information to the user.

According to embodiments, when connected to the modular hub, the modular components are in pneumatic communication with the pressurized gas supply and are in signal communication with the controller. The pressurized gas supply supplies a gas (e.g., air) to actuate the modular components when the components are connected to the modular hub, and the modular components retain the gas when the components are disconnected from the modular hub.

The modular components include a pneumatically-actuated, elastomeric, soft robotic gripper designed to apply direct pressure to the wound site, and a pneumatically-actuated tourniquet designed to apply pressure to limit blood flow to the wound site. Various embodiments of the present system include various-sized pneumatically-actuated, modular components that can accommodate different body sizes. The robotic gripper component utilizes a pneumatic system of fluid channels, or a pneumatic network generally termed "Pneu-Nets," that allows the gas to flow through the elastomeric material. In an embodiment, the soft robotic gripper replicates the direct pressure a medic would apply to a battlefield wound by hand (e.g., about one hundred eighty mmHg, or about three and one-half pounds per square inch (PSI)).

According to embodiments, the modular hub actively regulates the pneumatically-actuated, modular components by monitoring the amount of pressure being applied by the component, and actively increases or decreases the amount of pressure to obtain a determined pressure level. In an embodiment, the modular hub actively monitors the amount of pressure being applied by the gripper and instructs the system to maintain a determined pressure level. In an embodiment, the modular hub actively monitors the amount of pressure being applied by the tourniquet. Blood flow to the wound site is monitored and the modular hub instructs the system to maintain an appropriate pressure to the tourniquet that is enough to limit or stop blood flow to the wound site (e.g., about ninety to one hundred mmHg above the subject's systolic blood pressure). The present system minimizes the lasting nerve damage that typically results from the overtightening of tourniquets and/or their extended use for an excessive length of time. The system accomplishes this using a pressure regulation system with a pressure sensor that relays information back to a controller.

According to various embodiments, the present modular system includes a pressurized gas supply in pneumatic communication with the modular connections. The pneumatically-actuated, modular components are in pneumatic communication with the gas supply when they are connected to the modular hub, and the gas supply supplies the gas for actuating the modular components. In embodiments, the pneumatically-actuated, modular components retain the gas supplied to them by the gas supply when the components are disconnected from the modular hub.

According to various embodiments, the present system includes one or more sensors for measuring various parameters, such as a pressure sensor for measuring the pressure applied by the gripper and/or tourniquet, and a temperature sensor for measuring the temperature of the subject in the area around the wound site. The one or more sensors provide the modular hub and the controller with the information for a system feedback loop.

In various embodiments, the present system includes a display designed to provide system information to the user, such as the determined amount of pressure to be applied by the pneumatically-actuated, modular components, the current amount of pressure being applied, and the amount of time that pressure has been applied to the subject.

According to various embodiments, the present system includes a controller configured to control the various components of the system. The controller is in signal communication with the modular components that are connected to the modular hub, and in signal communication with the pressurized gas supply.

The present system includes components that come in contact with an open wound. Bacteria and contamination are an area of concern for infection. Some embodiments of the present system are configured for compliance with relevant FDA guidelines.

The present disclosure also relates to a method of treating a subject having a wound. Although not limited, the method generally applies to treating severe wounds, such as battlefield wounds that involve the immediate application of pressure to stem the bleeding, either by applying pressure directly to the wound site, or for more grievous wounds, by applying a tourniquet to stem the flow of blood to the wound site.

According to various embodiments, the present method utilizes the modular wound treatment system disclosed herein. The system includes a modular hub having a modular connection for one or more pneumatically-actuated, modular components. The one or more modular components include a pneumatically-actuated soft robotic gripper component designed to curve and at least partially encircle the wound site when actuated and thereby apply direct pressure to the wound site, and a pneumatically-actuated tourniquet component designed to apply pressure proximal to the wound site to limit or stop blood flow to the wound. The system also includes a pressurized gas supply in pneumatic communication with the modular connection, one or more sensors for measuring the pressure applied by the one or more pneumatically-actuated, modular components, a controller for controlling the system, and a display in signal communication with the controller designed to provide system information to the user.

In various embodiments of the method, one or more of the pneumatically-actuated soft robotic gripper and tourniquet components are applied to the subject. The gripper component is applied directly on the wound site, and the tourniquet component is applied proximal or upstream (based on the arterial blood flow) to the wound site. The gripper and/or tourniquet component is connected to the central modular hub, establishing a pneumatic connection with the gas supply and a signal connection with the controller. The robotic gripper and/or tourniquet components are then pneumatically-actuated with gas supplied by the pressurized gas supply such that the gripper actuates to apply an effective amount of direct pressure to the wound site to slow bleeding from the wound and/or the tourniquet applies an effective amount of direct pressure proximal to the wound site to stop or limit the flow of blood to the wound.

According to embodiments, the method also includes measuring the pressure being applied by the modular component and maintaining the pressure at, or adjusting the pressure to, a determined level that best suits the needs of the subject and the treatment of the wound.

While some embodiments of the present modular wound treatment system are designed to be utilized with subjects having a wound on a limb, and embodiment in the present disclosure are described or illustrated using a limb wound, the system is not so limited. Embodiments of the present modular system can be used to treat wounds on other body parts of the subject, such as the head, neck, chest and abdomen.

Other features and aspects of the invention will become apparent from the following detailed description, which taken in conjunction with the accompanying drawings illustrate, by way of example, the features in accordance with embodiments of the invention. This summary is not intended to identify key or essential features of the claimed subject matter, nor is it intended to limit the scope of the invention, which is defined solely by the claims attached hereto.

BRIEF DESCRIPTION OF THE DRAWINGS

An appreciation of the disclosure and many attendant advantages thereof may be understood by reference to the accompanying drawings. The attached drawings help explain the embodiments described below. Included in the drawings are the following figures:

FIG. 4A illustrates a top down perspective.

DETAILED DESCRIPTION

This detailed description, like the drawings, omits various details to help focus the reader's attention to the various points. A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

Terms and phrases used in this document, unless otherwise expressly stated, should be construed as open ended as opposed to closed—e.g., the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Furthermore, the presence of broadening words and phrases such as "one or more," "at least," "but not limited to," or other similar phrases, should not be read to mean that the narrower case is intended or required in instances where such broadening phrases may be absent. Any headers used are for convenience and should not be taken as limiting or restricting. Additionally, where this document refers to technologies that would be apparent or known to one of ordinary skill in the art, such technologies encompass those apparent or known to the skilled artisan now or at any time in the future.

According to various embodiments, the system is modular in order to adapt to various sized wounds, can sense and report temperature, pressure and/or time, and is corrosion resistant. Embodiments of the system include an alarm system that signals an operator of system functions and failures. In various embodiments, the system is portable and can be carried by one able-bodied person. Embodiments of the system can fit comfortably inside a rescue helicopter, such as a Blackhawk or Jayhawk helicopter. Various embodiments of the system involve minimal training and are designed to be used with and under duress with minimal instruction. Various embodiments of the system are designed to operate in harsh environments, such as a battlefield.

In embodiments, the system includes modular components that are sterile or sufficiently antiseptic to be in contact with open wounds. Embodiments of the system are compliant with U.S. Food and Drug Administration safety standards for emergency equipment. While in some embodiments, the modular components are designated for single use and/or are disposable, the central modular hub is reusable. According to various embodiments, the modular components are attached to the modular hub and pneumatically-actuated in a timely manner with regard to a trauma situation.

Various embodiments of the present system are able to sense and report the pressure being applied by the pneumatically-actuated, modular component to the wound site or the limb, the temperature of the wound and/or area around the wound (i.e., the site), the pulse and/or blood pressure of the subject, and the elapsed time that the modular component has been applied to the subject. This information is displayed on one or more digital displays.

In various embodiments, the system detects and identifies the particular pneumatically-actuated, modular component(s) that is connected to the modular hub. In embodiments, the digital display is configured to display which modular component(s) is connected to the system. If no component is connected, or the component is not recognized, the display shows no function. This lets the user know whether the system is functioning.

Figure 1:
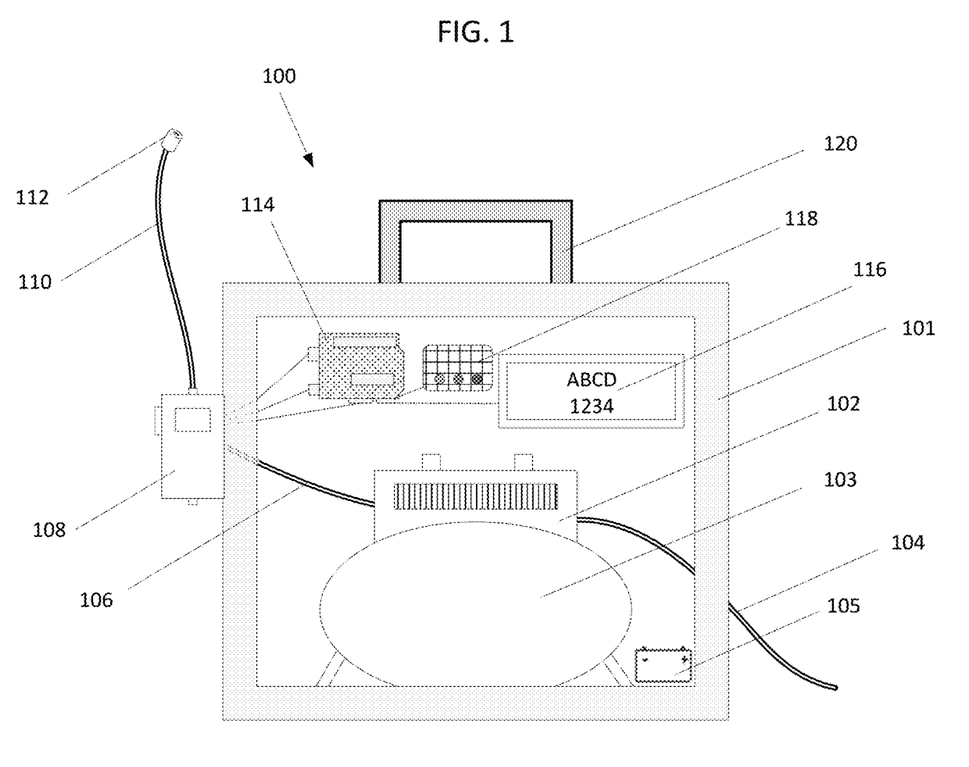
FIG. 1 schematically illustrates an embodiment of the present modular wound treatment system.

With reference to the drawing figures, FIG. 1 schematically illustrates an embodiment of the present modular system for treating wounds. The illustrated embodiment is not intended to be exhaustive or limit the present system to the precise form disclosed. It is chosen and described in order to explain the principles of the present system and method and its application and practical use, and thereby enable others skilled in the art to utilize the system and method.

According to various embodiments, a central, modular hub 100 actively regulates the pneumatically-actuated, modular components by monitoring the amount of pressure being applied by the component, and actively increases or decreases the amount of pressure to obtain a determined pressure level.

The modular hub 100 includes a unit housing 101, also referred to as a base unit housing in some embodiments. According to various embodiments, the unit housing 101 is constructed according to military standard General Requirements of Deployable Medical Standards (Mil-D-42048). Section 3.6 of the Requirements provides standards for containers, and specifies, for example, that the materials used in container design and construction shall be compatible with chemical agent decontamination, shall be corrosion resistant, dustproof, moisture vapor proof and provide protection to the contents from transit and storage damage due to vibration, shock or compression. The unit housing 101 also includes a handle 120.

According to various embodiments, the pressurized gas supply for pneumatically activating the modular components is a pneumatic pump, such as an air compressor 102. In some embodiments, the air compressor runs off of a DC power source, such as a battery 105 (e.g., a twelve or twenty-four-volt battery), or it runs off of AC, such as one hundred ten volts AC with a power cord 104, or it has the capability to run off of both. In some embodiments, the air compressor 102 normally runs off of AC power, but the power supply also includes a battery 105 to enable the air compressor to continue to temporarily operate in the absence of an external AC supply.

In some embodiments, the air compressor 102 includes a compressed gas storage tank 103 that is connected to the air compressor 102. In some embodiments, the air compressor includes a built-in gas pressure regulator. In other embodiments, the modular hub 100 externally includes a gas pressure regulator 108.

In response to control signals from a user, or from the controller 114, air compressor 102 operates to pressurize the gas storage tank 103. In some embodiments, the system includes a gas storage tank pressure transducer (not shown) pneumatically connected to the gas storage tank 103 and which generates a signal indicative of the pressure within the gas storage tank 103, which is communicated to the controller 114. Controller 114 activates the air compressor 102 to maintain the pressure in gas storage tank 103 near a predetermined level. It will also be appreciated that an external source of pressurized gas for the pressurization and activation of the pneumatically activated modular components can be provided to the system, eliminating the necessity for air compressor 102 and gas storage tank 103.

In an embodiment, the air compressor is the EPAuto twelve-volt DC Portable Air Compressor (model 705129800176; Walnut, Calif.). This air compressor uses a twelve-volt power supply (ten to fifteen amps) and provides up to one hundred to one hundred twenty pounds per square inch (PSI) of air, which is a sufficient amount of air to operate the present system. In another exemplary embodiment, the gas supply is a Greenworks twenty-four-volt Air Compressor (Model 41572; Mooresville, N.C.). This air compressor runs on a self-contained, twenty-four-volt battery, provides up to one hundred fifteen PSI, and features a half-gallon air tank to store compressed air.

In various embodiments, and as shown in FIG. 1, the air compressor 102 is contained within the unit housing 101 of the modular hub 100. Various embodiments of the system include a battery 105, such as a rechargeable twelve-volt battery, which is also contained within the unit housing 101 of the modular hub.

In various embodiments, the gas storage tank 103 has about a fifth of a gallon to one-gallon capacity, such as about half of a gallon. In one embodiment, the gas storage tank 103 is an AMP half-gallon basic aluminum air tank (Pacbrake, Blaine, Wash.). This air tank has a maximum working pressure of more than one hundred psi, such as about one hundred fifty to two hundred PSI. At one hundred fifty PSI, the half-gallon air tank holds a mass of air of about $2.3 \times 10^{-2}$ kg. According to embodiments, a half-gallon air tank holds enough compressed air to actuate at least about fifty to one hundred of the pneumatically-actuated, modular components.

According to other embodiments, the gas supply for pneumatically activating the modular components is a self-contained tank of compressed air or a carbon dioxide cylinder, in place of the air compressor. A compressed air cylinder or a carbon dioxide cylinder does not entail a power source such as that used to run an air compressor and provides a more compact and lighter system. This embodiment would operate well in a helicopter or battlefield setting in which a power source may not be readily available.

In some embodiments, the gas supply is a small compressed gas cartridge. In embodiments, the gas supply is a ten to thirty-gram carbon dioxide cartridge, such as a twelve, sixteen, or twenty-four-gram carbon dioxide cartridge. In embodiments, the small compressed air or carbon dioxide cartridge is intended for limited use, such as a single use, with the pneumatically activated modular component. The small compressed gas cartridge allows for increased mobility of the system, as the system is visualized to be used on helicopters and in battlefield situations. The cartridges are easily and quickly switched out when needed.

According to various embodiments, the gas supply or air compressor 102 supplies gas through an air hose 106 to a gas pressure regulator 108. The gas pressure regulator 108 is in fluid communication between a gas supply (i.e., air compressor 102 and/or gas storage tank 103) and the pneumatic air line 110. The gas pressure regulator 108 maintains the pressure in the pneumatically-actuated, modular component, when applied to a subject's limb or other location, near a determined reference pressure level. In an embodiment, the gas pressure regulator 108 maintains the pressure of the tourniquet component near a reference pressure level that is above a minimum pressure needed to limit or stop arterial blood flow past the tourniquet, for a determined length of time. In another embodiment, the gas pressure regulator 108 maintains the pressure of the soft robotic gripper component on the wound site near a pressure level that slows or stops the bleeding form the wound.

In various embodiments, the reference pressure level is set manually by a user, or it is determined automatically for an individual subject, or it adapts automatically during treatment. In some embodiments, the gas pressure regulator 108 is designed to maintain the modular component pressure within a predetermined pressure range from a reference pressure, and any fluctuations beyond that range are offset by actuation of the air compressor 102 or gas storage tank 103 to bring the modular component pressure back within the pressure range. For instance, if there is a pneumatic leakage sufficient to cause the modular component pressure to decrease beyond the predetermined pressure range, actuation of the gas pressure regulator 108 may bring it back within range, and if not, then a pressure-regulation alarm and/or display signal is produced.

According to various embodiments, the present system includes one or more pneumatic connections to the gas supply. The gas supply supplies the gas to actuate the pneumatically-actuated, modular components when the components are connected to the modular hub 100. Thus, the modular components are in pneumatic communication with the gas supply when the components are connected to the modular hub 100.

According to the embodiment shown in FIG. 1, the system includes one or more pneumatic air lines 110 that connect with the pneumatically-actuated, modular components. The pneumatic air line 110 is in pneumatic communication with gas through the gas pressure regulator 108. The pneumatically-actuated, modular components attach to the modular hub 100 through a quick connect connection 112 at an end of the pneumatic air line 110. In this manner, the pneumatically-actuated, modular components are in pneumatic communication with the gas supply, i.e., the air compressor 102 and/or compressed gas storage tank 103, when the components are connected to the modular hub 100. Embodiments of the present system include two or more pneumatic air lines 110 for connecting with at least two pneumatically-actuated, modular components, wherein the at least two pneumatically-actuated, modular components can be simultaneously connected to the modular hub.

According to various embodiments, the system can have more than one gas pressure regulator 108, each separately supplying gas to a single pneumatically-actuated, modular component. In other embodiments, just one instance of the gas pressure regulator 108 supplies gas to multiple pneumatically-actuated, modular components.

According to various embodiments, the present modular wound treatment system includes a controller 114, which acts as the brain of the system. In embodiments, the controller 114 is a microcontroller typical of those known in the art with associated memory, analog and digital peripheral interface circuitry, and other support components. Controller 114 executes software programs that control the operation of the system as described herein.

In one embodiment, the controller 114 tracks the amount of time that has elapsed since the system was applied to the subject and the components have been pneumatically-actuated. In embodiments, the controller 114 also monitors the subject's temperature at the wound site and receives readings of the subject's blood pressure taken by a measuring device. The controller also sends such related information to a display 116.

In various embodiments, the controller 114 includes an Arduino board (Turin, IT). Arduino is an open-source hardware and software company, project and user community that designs and manufactures single-board microcontrollers and microcontroller kits for digital devices. Its products are licensed under the GNU Lesser General Public License (LGPL) or the GNU General Public License (GPL), permitting the manufacture of Arduino boards and software distribution by anyone. Arduino boards are available commercially in preassembled form or as do-it-yourself kits. Arduino board designs use a variety of microprocessors and controllers. The boards are equipped with sets of digital and analog input/output (I/O) pins that may be interfaced to various expansion boards or breadboards (shields) and other circuits. The boards feature serial communications interfaces, including Universal Serial Bus (USB) on some models, which are also used for loading programs from personal computers. The Arduinos are programmed using C and C++. In addition to using traditional compiler toolchains, the Arduino project provides an integrated development environment (IDE) based on the Processing language project.

In some embodiments, the controller 114 is the Arduino Uno microcontroller board, which is based on the Microchip ATmega328P microcontroller. The board is equipped with sets of digital and analog input/output (I/O) pins that can be interfaced to various expansion boards (shields) and other circuits. The board has fourteen digital pins, six analog pins, and is programmable with the Arduino IDE (Integrated Development Environment) via a type B USB cable. It can be powered by the USB cable or by an external, nine-volt battery, though it accepts voltages between seven and twenty volts. In other embodiments, the controller 114 is the Arduino Due microcontroller board, which is based on the Atmel SAM3X8E ARM Cortex-M3 CPU and has twelve analog inputs, or the Arduino Mega, which is based on the ATmega2560 and has sixteen analog inputs.

According to various embodiments, the controller 114 recognizes the type of pneumatically-actuated, modular component that is connected to the modular hub 100. The controller 114 recognizes the modular component, for instance the soft robotic gripper component or the tourniquet component, by recognizing the input voltage or current flow when the component is plugged in.

In some embodiments, the controller 114 is an Inter-Integrated Circuit (I2C), which is a synchronous, multi-master, multi-slave, packet switched, single-ended, serial computer bus. I2C provides addresses to components, i.e., the pneumatically-actuated, modular components, so that the driver can identify which component is plugged into the modular hub 100. If more than one modular component is plugged in, for instance, a robotic gripper and a tourniquet, each has its own identity and I2C will distinguish between the components' respective identities and run the applicable code.

According to various embodiments, a microcontroller is installed into one or more or all the modular components. The microcontroller is, for example, an Arduino Nano, which is a small, complete and breadboard friendly board based on the ATmega328P. In this manner, the system continues to interpret data from the sensors even when the modular component is disconnected from the modular hub. In an embodiment, an installed microcontroller in the soft robotic gripper continues to keep track of the amount of pressure the gripper is applying to the wound even when disconnected from the modular hub. In an embodiment Arduino code is uploaded to the individual modular component based on the need for continuous operation.

According to various embodiments, the modular hub 100 includes a display 116. The display 116 shows relevant information and feedback to the operator, such as the amount of pressure to be applied by the pneumatically-actuated, modular components, the current amount of pressure being applied, the amount of time that pressure has been applied to the subject, or instructions for operation of the system. In some embodiments, the display 116 also shows the temperature of the subject in the wound area being treated and the blood pressure and/or pulse rate of the subject. Some embodiments include a mode switch that allows the user to select which of the relevant information is shown on the display 116.

According to some embodiments, the display 116 is an LED display, such as a four-line LED display unit from Newhaven Display International (Elgin, Ill.) or a 20×4 LCD module with a built-in shield from SunFounder. In various embodiments, the display 116 will give the operator visual feedback for the status of the device and system as it applies pressure to the one or more pneumatically-actuated, modular components. The display 116 shows one or more of: the time elapsed since the pneumatically activated modular component was applied to the subject, the pressure that the component is applying to the subject, the heart rate of the subject, the blood pressure of the subject, the temperature of the subject in the area around the wound. This allows the user to observe the effects of the pneumatically-actuated, modular components on the subject.

According to various embodiments, the present modular wound treatment system includes an alarm system that signals and alerts the user to various circumstances. The alarm system includes an audible and/or visual indication of various conditions. The controller 114 activates the alarm system under certain predetermined conditions of pressure and elapsed inflation time.

In an embodiment, the system includes an alarm 118 that signals or alerts the user when the gas supply is running low. In another embodiment, the alarm 118 signals or alerts the user when the pneumatically-actuated, modular component is running low on air or loses pressure. In another embodiment, the alarm 118 notifies the user when the modular component has been actuated and applied to the patient for a determined length of time. In another embodiment, the alarm 118 signals or alerts the user when the pressure applied by the modular component is too high or too low (e.g., higher or lower than a determined reference pressure). In another embodiment, the alarm 118 is activated if unusually high pressures are detected in the pneumatically activated modular component (e.g., above four hundred mmHg in the tourniquet component) to alert the user that the pressure may be higher than needed and may be unsafe to the subject.

In embodiments, the alarm 118 notifies the user when the pressure applied by the robotic gripper or tourniquet is too high or too low. In another embodiment, if the tourniquet component has been pneumatically activated and pressurized above a predetermined threshold and has remained above this threshold continuously for a predetermined elapsed time, alarm 118 is activated to notify the user to deflate the tourniquet for a reperfusion period of 5 to 10 minutes to reduce the extent of avoidable ischemic damage to the limb. A suitable elapsed time is 2 hours, suggested in the art as a generally safe period for continuous occlusion in a limb.

According to various embodiments, as the pneumatically-actuated, modular component loses pressure, the alarm 118 includes a flashing yellow light to remind the user to apply additional gas from the gas supply. If the modular component loses a substantial amount of pressure, then the alarm 118 includes a flashing red light to alert the user of an urgent need to apply additional gas from the gas supply. If the pressure is within a correct determined range, the alarm 118 provides a green light to notify the user that everything is satisfactory. In any embodiment, the alarm also includes an audible alarm signal.

In some embodiments of the system, the pneumatically-actuated, modular component continues to function when disconnected from the modular hub 100, and the system continues to keep track of the current pressure, temperature and/or time. If the component loses pressure, the alarm 118 notifies the user to reattach the component to the modular hub 100.

According to various embodiments, the present system contains a connection subsystem that allows for quick connection and disconnection of the pneumatically-actuated, modular components. The "quick connect" system is also designed to allow for free air flow when the component is connected to the modular hub but to prevent air flow when there is no connection. The quick connect system is universal for the modular system so that the pneumatically-actuated, modular components utilize the same quick connection system. This is another aspect of the present modular system.

Figure 2A:
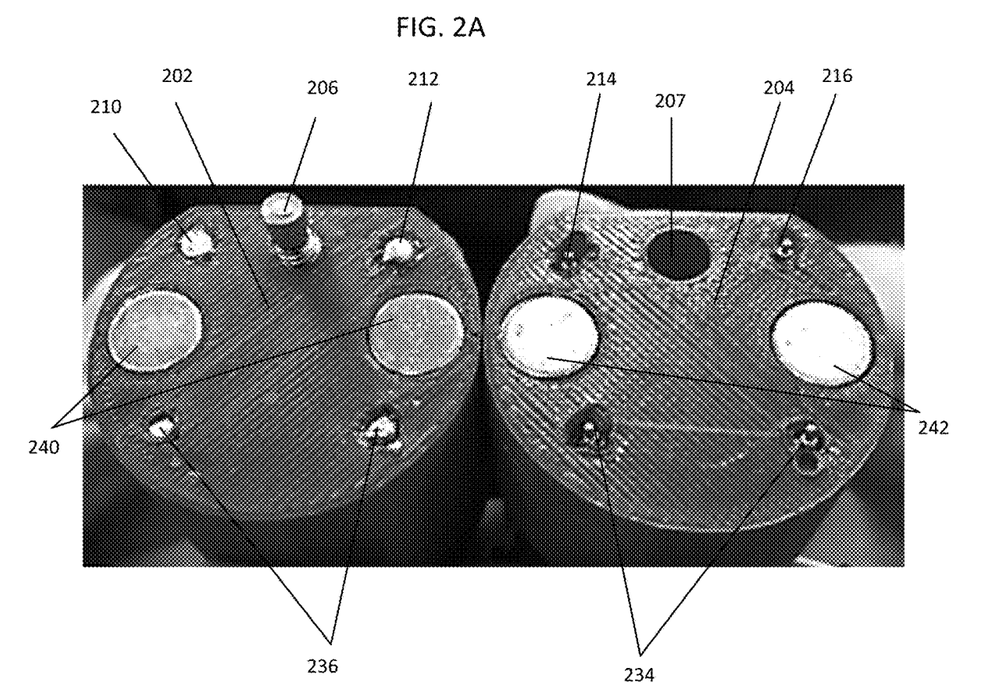
FIG. 2A shows two coordinating body components (i.e., male and female) of the quick connection system for the pneumatically-actuated, modular components according to an embodiment of the disclosure.
Figure 2B:
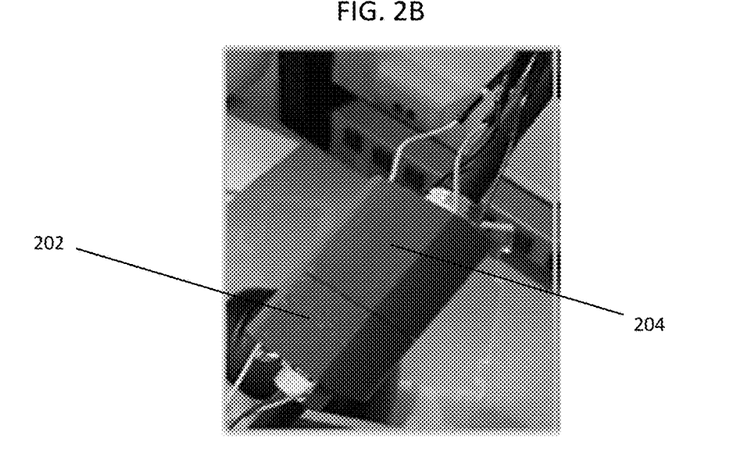
FIG. 2B shows the two body components magnetically connected and held together, establishing a pneumatic and signal connection through the two body components.

According to embodiments illustrated in FIG. 2A and FIG. 2B, the quick connect system includes a pair of coordinated or matching body components 202 and 204, often referred to as a male/female connector pair, which together provide a magnetic quick connector. The components of the quick connect system also include a check valve 206, a pneumatic connection 207 corresponding with the check valve, and electrical contacts 210, 212, 214, 216. The check valve 206 allows for the modular component, such as the soft robotic gripper or tourniquet, to cut off air flow and maintain the pressure that has been applied to the component once it has been disconnected from the modular hub. In various embodiments, the check valve 206 utilizes one or more Presta valves that allow air to flow freely when the internal pin of the valve is compressed and prevents air flow when the pin is extended. The check valve 206 on body component 202 pairs with the pneumatic connection 207 on body component 204, and together they form a pneumatic communication between the pneumatically-actuated, modular component, the pneumatic air line 110, gas pressure regulator 108, air hose 106, and gas supply (e.g., air compressor 102 and/or gas storage tank 103).

According to various embodiments, the quick connect system utilizes a magnetic connection system. Embodiments utilize one or more magnets 240, 242 and a magnetic interface to hold a connection between the two body components 202, 204, which then holds the pneumatic and signal connection between the gas supply the modular hub 100 and the modular component. As shown in FIG. 2B, the magnets 240, 242 ensure that both ends of the body components 202, 204 are firmly secured to one another but allow for fast and easy disconnection.

Figure 3:
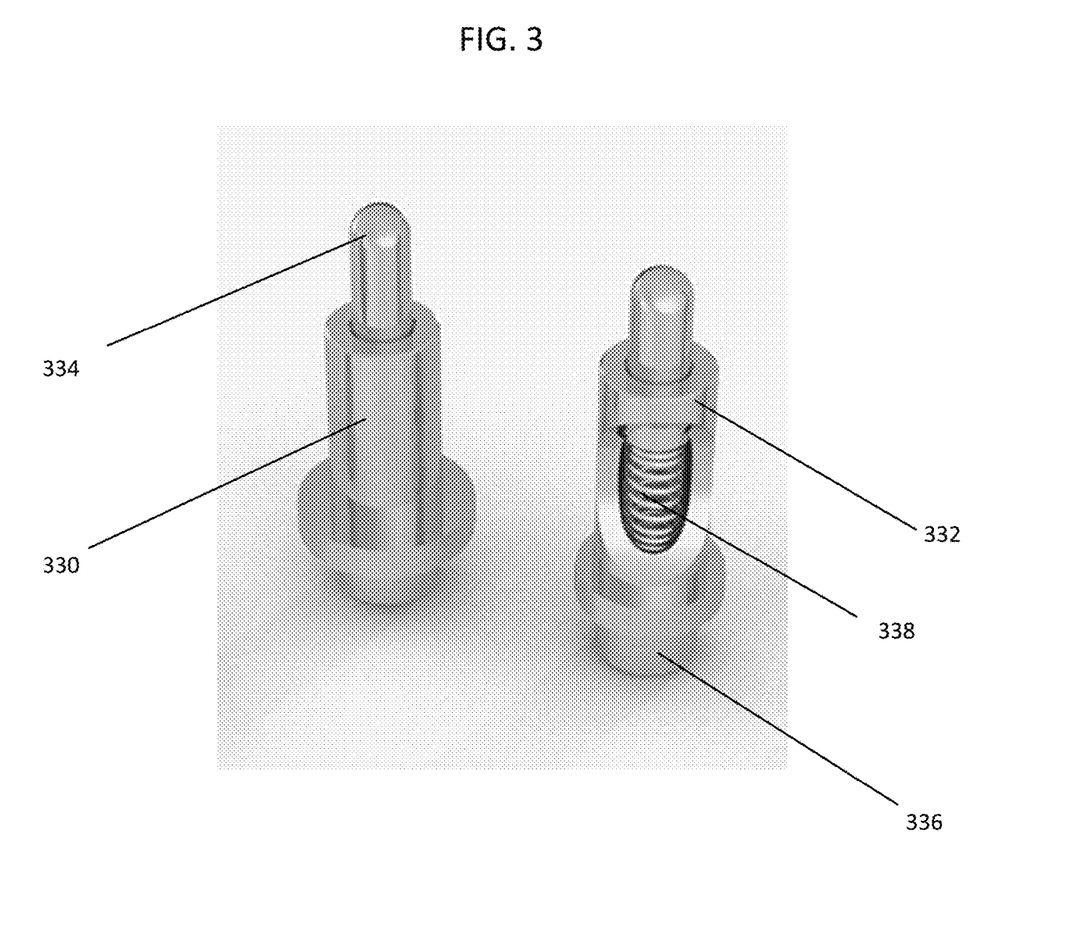
FIG. 3 illustrates the spring-loaded pin connectors utilized in an embodiment of the quick connection system.

According to various embodiments, the quick connect system also includes an electrical connection involving the electronics that allow the modular hub 100 to send and receive signals to and from the pneumatically-actuated, modular components. The electrical connection includes one or more electrical contacts 210, 212, 214, 216 for relaying signals and/or electricity for the sensors. In various embodiments, the electrical contacts utilize spring loaded pin connectors 330, 332 with male ends 334 and female ends 336, as shown in FIG. 3. When the two ends make contact, it allows for a signal to be sent through the physical connection, and the springs 338 allow quick connection and disconnection of the electrical system.

According to various embodiments, the one or more pneumatically-actuated, modular components includes a soft robotic gripper, designed to provide a similar type of pressure to a wound that a person would provide if applying pressure to a wound site with their hands. In general, the gripper is applied to light or moderate wounds so that the caretaker can effectively triage a patient while attending to their wounds.

In embodiments, the soft robotic gripper is made of an elastomeric material that has a pneumatic network of inner cavities and channels running through it (pneu-nets). The pneu-nets allow and restrict gas flow to chosen parts of the gripper component. The design of the channels along with the chosen materials (materials have varying elongation and flexibility) determine how the gripper component will react to a gas filling the inner cavities. According to various embodiments, the pneu-nets allow the gripper to have a bending action that is created when the component is actuated by introducing gas or air into the gripper. Activating the pneu-nets causes the gripper to bend and curve in a predetermined manner to at least partially encircle a subject's limb and apply direct pressure to the limb.

In various embodiments, the soft robotic gripper includes a plurality of chambers made of an extensible or elastomeric material, the chambers having interior side walls and exterior walls, at least a portion of the interior side wall being separated from an interior side wall of an adjacent chamber. A channel fluidically interconnects the plurality of chambers, and the interior walls are configured to be more compliant than the exterior walls. The gripper also has a strain limiting base, which in some embodiments includes an inextensible flexible layer. The gripper further includes an inlet port for receiving a pressurizing fluid or gas.

Figure 4A:
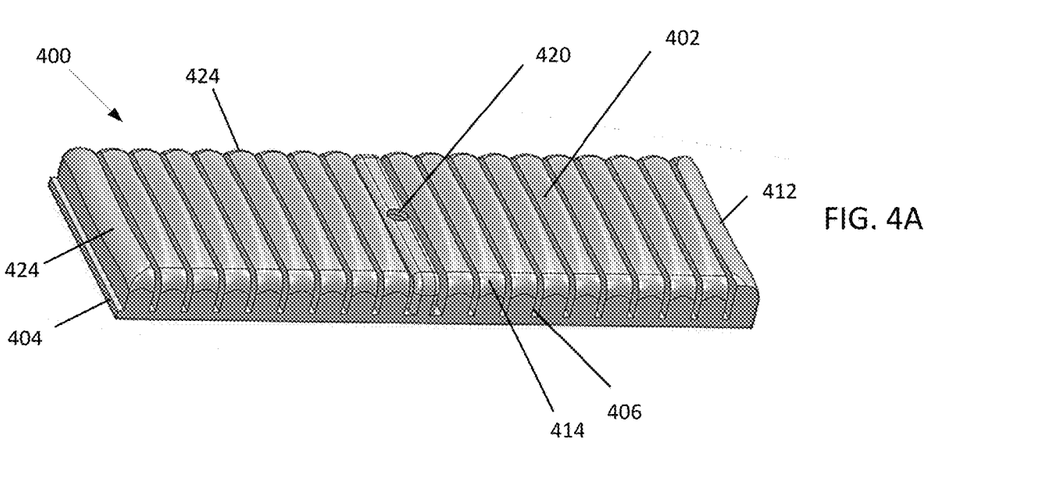
Figure 4B:
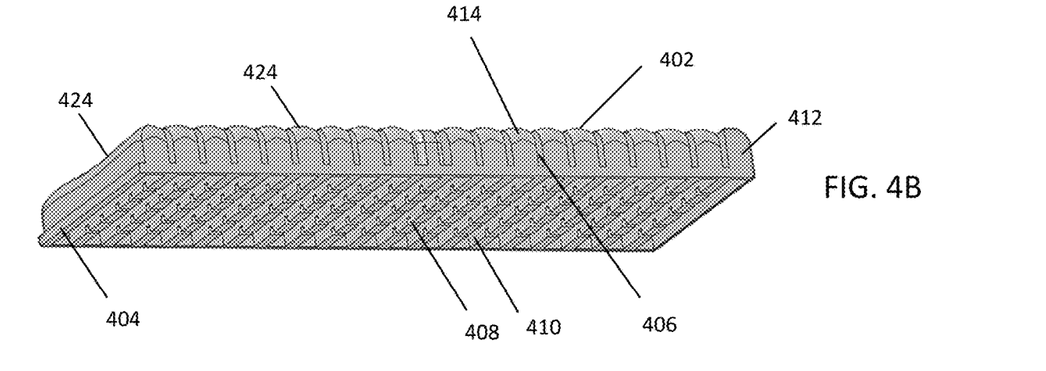
FIG. 4B illustrates a bottom up perspective, of a pneumatically-actuated soft robotic gripper component according to an embodiment of the disclosure.

According to various embodiments, FIG. 4A and FIG. 4B are upper and lower perspective views of a soft robotic gripper pad 400 having twenty chambers 402, that are flexible and elastomeric, secured in common to base 404. The chambers 402 are unsupported and have interior side walls 406 that are not connected to the interior side walls of its neighboring chamber(s). In various embodiments, the interior side wall has greater than 25%, greater than 50%, or greater than 75% of its surface area that is not connected to the interior side wall of its neighboring chamber.

The chambers 402 are fluidically connected, for example, through a network of conduits 408, 410 located near the base of the chambers 402. The chambers 402 have interior side walls 406, exterior walls 412 and top walls 414. In one or more embodiments, the exterior walls 412 and/or top walls 414 are stiffer and/or thicker than the interior side walls 406. In some embodiments, the greater stiffness of the exterior walls 412 and the increased extensibility of the interior side walls 406 is accomplished by using different materials for exterior and interior walls. As shown in FIG. 4A and FIG. 4B, the soft robotic gripper pad 400 has chambers 402 with top walls 414 that have rounded and curved outer edges 424.

The chambers 402 are secured to a base 404 that is inextensible, less extensible, or strain limiting, and that resists expansion when the chambers are pressurized. In some embodiments, the base 404 is made of a material having a higher elastic modulus than that of the chambers 402. The higher modulus material provides a base 404 where inflation is not desired, while the low elastic modulus material is used for the chambers 402 where extensibility is needed. In other embodiments, the base 404 includes an inextensible material, such as paper or fabric, embedded in the base.

The soft robotic gripper pad 400 includes a gas inlet port 420 that is fluidically interconnected with the network of conduits 408, 410 and the plurality of chambers 402. Embodiments of the gripper pad will include a valve connected to the gas inlet port 420.

In some embodiments, to achieve a similar result as a human applying pressure to a wound site, the actuated gripper exerts between about one to five PSI of pressure (about fifty-two to two hundred sixty mmHg) to the affected area. In some embodiments, the gripper applies even more pressure, for example, over six PSI of pressure.

In various embodiments, the soft robotic gripper is made from thermoplastic polyurethane (TPU). The TPU can withstand very high pressure (e.g., greater than 1000 PSI) without losing its form. In various embodiments, the soft robotic gripper is constructed by 3D printing, using, for example, a LulzBot Taz 6 3D printer (Loveland, Colo.). In some embodiments, the 3D printer also includes an Aerostruder tool head, which incorporates a centrifugal fan and quad-port cooling duct for three-hundred-sixty-degree part cooling.

When the soft robotic gripper is inflated, embodiments of the gripper maintain the gas and gas pressure when the gripper is disconnected from the modular hub and the gas supply. According to various embodiments, the robotic gripper is tested for air worthiness according to ASTM Standard Test Method for Determination of Leaks in Flexible Packaging by Bubble Emission (ASTM D3078-02). In other embodiments, the robotic gripper is tested for air worthiness by submerging a pressurized gripper in a large bucket of warm water and noting the presence and location, or absence, of air bubbles, which indicate leakage.

According to various embodiments, the pneumatically-actuated modular tourniquet component of the present system is designed to be applied to the subject above the location of (proximal to) the wound site, to restrict arterial blood flow to the wound. Embodiments of the system include an automated "smart tourniquet" that minimizes lasting nerve damage that typically results from the over-tightening of tourniquets. When connected to the modular hub of the present system, the tourniquet will apply a minimum amount of pressure to restrict arterial blood flow and will not apply excessive pressure. This ensures the effectiveness of the tourniquet while preventing unnecessary pain or tissue damage to the subject.

Pneumatic tourniquets have been proven to be effective and safe devices for reducing or stopping arterial blood flow and represent a standard of care in modern surgery and trauma treatment. When a pneumatic tourniquet is in use, an inflatable bladder encircles the limb and is inflated, causing the bladder to expand and apply inward radial compression to the limb around the limb circumference. Pneumatic tourniquets apply pressure to the limb that is very closely related to the inflation pressure of the bladder, and this pressure is applied evenly around the entire limb circumference. It is therefore easy to control the pressure applied to the limb by monitoring the tourniquet inflation pressure, and low-pressure areas are minimized. A pneumatic tourniquet is snugly applied around the limb and secured at a fixed circumference to be most effective.

Figure 5:
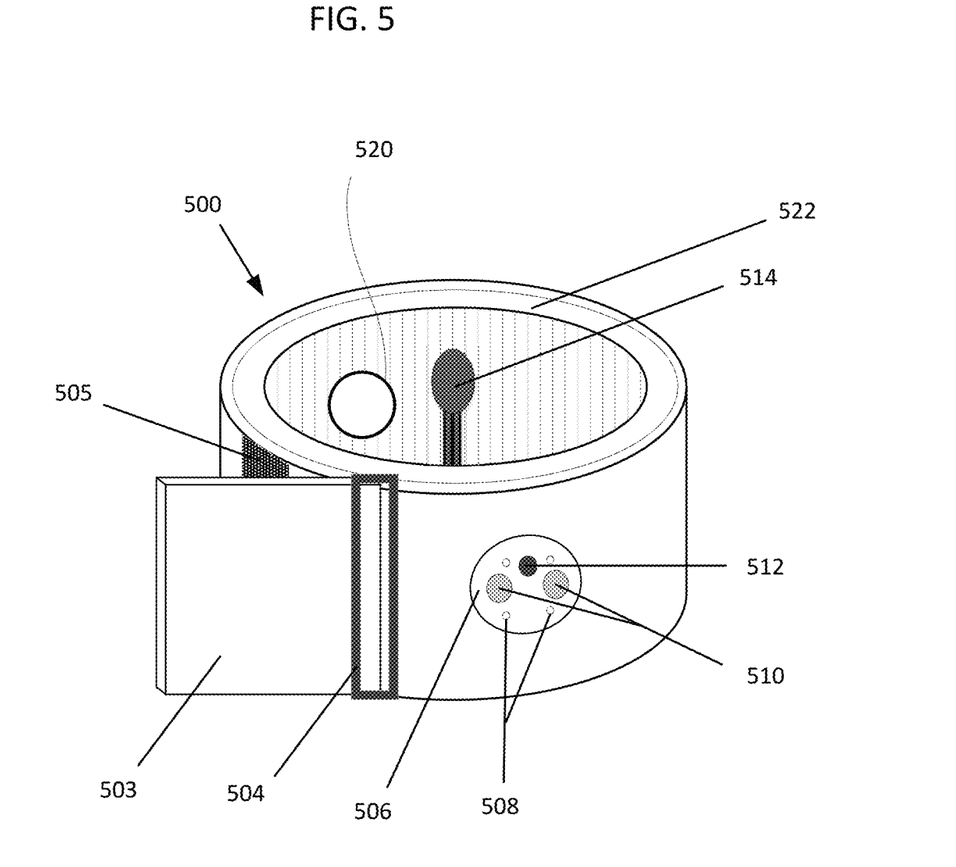
FIG. 5 illustrates a pneumatically-actuated tourniquet component according to an embodiment of the disclosure.

Illustrated in FIG. 5, embodiments of the tourniquet 500 include a cuff 502, a pneumatic tourniquet cuff. The tourniquet 500 has a cuff 502 that is longer in circumference of the limb to be occluded with the cuff, such that the cuff 502 overlaps upon itself when wrapped around the limb. In various embodiments, the amount of overlap 503 is about 1 to 5 inches, and typically the appropriate size of cuff 502 is selected and wrapped around the limb and secured by a buckle 504 and hook and loop type fastening straps 505.

In various embodiments, the cuff 502 is formed of plastic coated fabric materials that can be sterilized by techniques normally used to sterilize medical devices. Cuff 502 is also formed of material that can withstand multiple cleaning and disinfection cycles by techniques normally used to clean and disinfect medical devices.

The tourniquet 500 also includes one of a matching pair of quick connector body components 506 of the quick connect system. The quick connector body component 506 is paired with a counterpart body component such as body component 202 or body component 204 of the quick connect connection 112 for attachment to the pneumatic air line 110 and ultimately pneumatic communication with the gas supply (e.g., air compressor 102). The quick connector body component 506 includes one or more electrical contacts 508, one or more magnets 510, and a check valve 512. Embodiments of the tourniquet 500 connect to the modular hub 100 via the quick connection system of the present disclosure.

In some embodiments, the tourniquet 500 includes a temperature sensor 514, such as a thermistor or thermocouple, adapted to accurately measure the temperature of the subject at the wound location. The temperature sensor 514 relays the temperature back to the controller 114 and the display 116.

According to various embodiments, the tourniquet 500 includes a display panel (not shown) for the selective display of any of the following information: the level of pressure within cuff 502 (cuff pressure); determined tourniquet cuff pressure; the pressure level to be maintained in cuff 502 when cuff is pressurized (reference pressure level); pressure warning indicators; menus of user selectable commands for the operation of the tourniquet.

Studies have shown that a safe and effective tourniquet pressure is the lowest cuff pressure that will stop the penetration of arterial blood past the cuff. Such studies have shown that higher tourniquet pressures are associated with higher risks of tourniquet-related injuries to the patient. A guideline for setting the pressure of the tourniquet is based on the "Limb Occlusion Pressure" (LOP), which can be defined as the minimum pressure required, at a specific time in a specific tourniquet cuff applied to a specific patient's limb at a specific location to stop the flow of arterial blood into the limb distal to the cuff. LOP is affected by variables including the patient's limb characteristics, characteristics of the tourniquet cuff, the application of the cuff to the limb, physiologic characteristics of the patient including blood pressure and limb temperature, and other factors such as the elevation of the limb and limb movement.

When in use according to various embodiments, the pneumatically-actuated tourniquet component applies pressure about fifty to seventy-five mmHg above the determined LOP. The LOP is estimated, or it is measured, such as via palpation or pulse oximeter. In embodiments, the pneumatically-actuated tourniquet component applies about one hundred fifty to three hundred mmHg, about one hundred seventy to three hundred mmHg, about one hundred eighty to three hundred mmHg, or about two hundred to three hundred mmHg of cuff pressure to the subject.

According to various embodiments, the controller 114 receives a cuff pressure signal indicative of the pressure within the cuff 502. The cuff pressure signal is communicated to the gas pressure regulator 108 by the controller 114. Typical in the art, the pressure within cuff 502 is measured and expressed in units of mmHg. In various embodiments, the cuff pressure signal is received from a pressure transducer (not shown) pneumatically connected to the cuff 502. In some embodiments, the transducer is incorporated into the cuff 502.

In embodiments, when enabled by controller 114, gas pressure regulator 108 operates to maintain the pressure in cuff 502 (cuff pressure) near the reference pressure level. Gas pressure regulator 108 responds to a difference in pressure between the reference pressure level and the cuff pressure caused by transient volume changes in cuff 502 due to movement or manipulation of the limb, or to leakage from the cuff 502, and add to or remove gas from the cuff 502, thereby maintaining the cuff pressure near the reference pressure level.

If, at times, the gas pressure regulator 108 cannot maintain the cuff pressure within the determined operating limits, controller 114 will indicate a high or low pressure alarm condition to the user via a user interface. The alarm 118 can be audible or visual. For instance, in an embodiment, an alarm is indicated if the cuff pressure cannot be maintained at a level of plus or minus fifteen mmHg of the reference pressure level. It will be appreciated that other regulation limits can be selected.

In various embodiments, the reference pressure level is set to pressure values that are equal to or below a normal safe pressure limit, for example, about two hundred mmHg, and sets the initial value of the reference pressure level to a value that does not exceed a normal safe pressure level. Setting the reference pressure level higher than the normal safe pressure limit may be done in some circumstances to occlude blood flow, such as when the subject is very obese.

The use of higher cuff pressures is associated with higher risk of injury to the subject. To reduce the risk of the user applying a pressure level that is too high, in some embodiments the controller 114 will not permit the reference pressure level to exceed a predetermined maximum limit, for example, about six hundred mmHg.

In various embodiments, the duration of inflation of the tourniquet is monitored, and the length of time is shown on the display 116. A common recommendation that a tourniquet can remain safely inflated is two hours, which is based on the finding that cellular ischemic changes such as mitochondrial swelling, myelin degeneration, glycogen storage depletion and Z-line lysis are reversible if the tourniquet is inflated for no more than two hours. The deleterious effects of tourniquet inflation include pain while the tourniquet is inflated ("tourniquet pain"), metabolic and hemodynamic changes that occur during tourniquet inflation and deflation, damage to blood vessels and muscle, and perioperative neuropathy if the tourniquet is inflated for excessive periods.

According to various embodiments, the present system includes one or more pressure sensors 520 (FIG. 5) adapted to measure the amount of pressure applied by pneumatically-actuated, modular components, such as the gripper component and the tourniquet component. In some embodiments, the component will include three pressure sensors. According to various embodiments of the system, the pneumatically-actuated, modular components, such as the gripper component will apply about two hundred thirty mmHg (about four and one-half PSI) of pressure, and the tourniquet component will apply about one hundred sixty to two hundred ninety mmHg (about three to five and six tenths PSI) of pressure during operation and pneumatic activation.

In some embodiments, the pressure sensor is the FLEXIFORCE™ A401 Sensor (Tekscan, Boston, Mass.), which has a sensing area of about 25.4 mm (one inch), a 2-pin connector and a force range of about 111 N (0-25 pounds). The pressure sensor acts as a resistor and has a different resistance value based on the amount of force being applied to it. The FLEXIFORCE™ sensor decreases in resistance as the load being applied increases.

The dynamic range of the A401 sensor can be modified by changing the drive voltage and adjusting the resistance of the feedback resistor. In general, to measure higher forces, a lower drive voltage (negative one-half volt, negative one-quarter volt, etc.) is applied, and the resistance of the feedback resistor is reduced (one kilo-ohm min.). To measure lower forces, a higher drive voltage is applied, and the resistance of the feedback resistor is increased. According to embodiments, the pressure sensor is calibrated to accurately relay the pressure applied back to the controller, which will determine if enough or too much pressure is being applied.

As the pressure sensor feeds information back to the controller 114, the controller in turn shows the data from the sensor on a display 116, such as a four-line LCD screen. This allows the operator to observe the effects of the pneumatically-actuated, modular components on the subject.

In various embodiments, the pressure sensor is installed in the pneumatically-actuated, modular component using an adhesive, such as a rubber adhesive, for example, ECOFLEX™ 00-30. This provides a thorough seal against the skin, while allowing the pressure sensor to deliver accurate readings to the modular hub.

There is generally a slight variance between individual sensors. Thus, according to various embodiments, the pressure sensor is calibrated and conditioned before initial use.

In some embodiments, the pressure sensor is calibrated before every use. Calibration helps improve repeatability and neutralize drift.

In embodiments, the system is conditioned to "break in" the sensor before calibration and before every use. The sensor is conditioned by applying about one hundred ten to one hundred twenty percent of the expected maximum load onto the sensor for approximately three seconds. The load is then removed from the sensor and the process is repeated four to five times. The sensor is then calibrated.

In an embodiment, the pressure sensor is calibrated by the following procedure.

First, place a first test weight on the sensor. Leave the weight on the sensor for the same amount of time before recording the output; this helps minimize the drift error. Record the output, then remove the weight from the sensor.

Second, place a second test weight on the sensor, again waiting the same amount of time, and record the output. Remove the weight.

Third, place a third test weight on the sensor, wait the same amount of time and record the output. A further two through five sets of data or more can be collected with additional test weights. Gather the sets of data and plot the data on a graph (Sensor Output vs Force applied), which gives a linear plot, and calculate a best fit line. Additional embodiments utilize a FLEXIFORCE™ OEM development kit (Tekscan) for data analysis and calibration.

Figure 6:
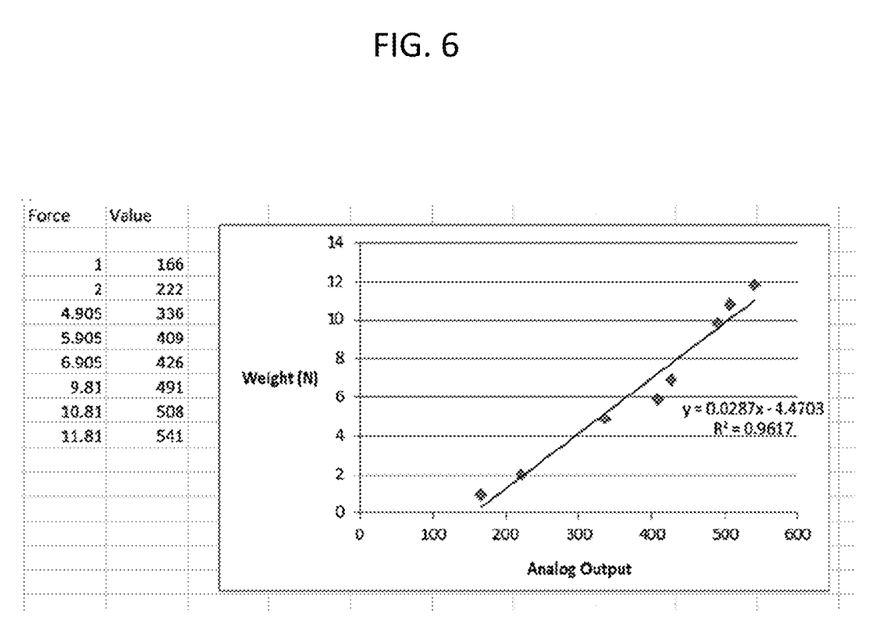
FIG. 6 is a graph to show a pressure sensor calibration according to an embodiment of the disclosure.

The results of an exemplary pressure sensor calibration example are shown in FIG. 6. The test weights consisted of two five-hundred-gram and two one-Newton weights. The analog output of the sensor was read and graphed versus its corresponding force in Newtons. A best fit line and equation was calculated, and 0.0287, or the slope of the line, was determined to be the calibration factor for the sensor, with a bias of 4.47 subtracted from the output.

According to various embodiments, the present system includes a temperature sensor (e.g., 514 in FIG. 5) that measures the temperature of the wound and/or the area around the wound. Furthermore, additional embodiments of the system include a mechanism for cooling the wound while the pneumatically-actuated, modular components are in place. Keeping the wound cool prolongs the life of the tissue and nerves around the wound.

Some embodiments of the system utilize a thermistor, such as a negative temperature coefficient (NTC) thermistor. A NTC thermistor is a nonlinear resistor; therefore, the resistance of the thermistor will change with the temperature that it is sensing. The resistance of the thermistor will decrease as the temperature around the thermistor increases. In one or more embodiments, the temperature sensor is a NTC thermistor from Ametherm (Carson City, Nev.).

Some embodiments of the system utilize a thermocouple, such as a T-Type thermocouple. In one or more embodiments, the temperature sensor is a T-Type thermocouple from ReoTemp Instruments (San Diego, Calif.). The thermocouple is supported by an Arduino shield, such as a SainSmart MAZ6675 module (Lenexa, Kans.), in combination with the controller. As the thermocouple sensor feeds information back to the controller 114, the controller in turn shows the data from the sensor on the display 116, such as an LCD screen. This allows the operator to observe the effects of the pneumatically-actuated, modular components on the subject.

One difference between a thermocouple and a thermistor is that a thermistor requires a constant current to operate, which will produce a greater draw on the power source, whereas a thermocouple measures a voltage difference to operate, which requires less power. When working with a thermocouple shield, the temperature sensor may be less responsive than with a thermistor, which reads the change in voltage directly from the sensor. However, the thermocouple may produce more consistent steady state temperatures because of less noise when going through the thermocouple shield.

In various embodiments, the temperature sensor is installed in the pneumatically-actuated, modular component using an adhesive, such as a rubber adhesive, for example, ECOFLEX™ 00-30. This provides a thorough seal against the skin, while allowing the thermistor or thermocouple to deliver accurate readings to the modular hub.

According to various embodiments, the system includes a blood pressure monitor, such as a cuff, to measure the subject's blood pressure. Various embodiments of the blood pressure monitor are well known to those of skill in the art. The blood pressure monitor sends a reading to the controller 114, which then sends the reading to a display 116. In various embodiments, the controller 114 will utilize the blood pressure reading to actively control the amount of pressure to be applied to the pneumatically-actuated, modular components, such as the tourniquet component. In some embodiments, the controller 114 actively controls the amount of pressure to the tourniquet component in order to maintain pressure of a determined amount above the subject's systolic blood pressure, such as about ninety to one hundred mmHg above the systolic pressure. In various embodiments of the system, the blood pressure cuff is located on the same or a different appendage of the subject as that of the wound.

According to various embodiments, the modular system is designed to recognize the different connections of the pneumatically-actuated, modular components. The system includes a coded controller 114 that ties together the circuitry of the system and ties together the circuitry of the modular components. The circuits, along with the code, allows the controller 114 to recognize different electronic connections.

Although the various embodiments of the present wound treatment system have been described primarily for use with treating wounds on limbs (arms and legs), the present system is not so limited. Embodiments of the system are used to treat other areas of the body, such as the head and scalp, chest, abdomen, hands and feet. For instance, the pneumatically-actuated tourniquet component is applied to the patient head to prevent the flow of arterial blood into a region of the scalp.

According to various embodiments, a method of treating a subject who has a wound is disclosed. The method utilizes the system disclosed herein. In embodiments, the method includes providing a modular wound treatment system that includes a modular hub having a modular connection for one or more pneumatically-actuated, modular components. The modular components include one or more of a pneumatically-actuated soft robotic gripper component having a pneumatic network of channels and chambers, the gripper component configured to curve and at least partially encircle the wound site when actuated and thereby apply direct pressure to the wound site, and a pneumatically-actuated tourniquet component configured to apply pressure proximal to the wound site to limit blood flow to the wound. The system also includes a gas supply in pneumatic communication with the modular connection, one or more sensors for measuring the pressure applied by the one or more pneumatically-actuated, modular components, a display designed to provide system information to a user, and a controller for controlling the system. In various embodiments, the modular components are in pneumatic communication with the gas supply when the components are connected to the modular hub, the gas supply supplies a gas to actuate the modular components when the components are connected to the modular hub, the modular components retain the gas supplied to them by the gas supply when the components are disconnected from the modular hub, the soft robotic gripper component is configured to curve and at least partially encircle the wound when actuated, and the modular components are in signal communication with the controller when the components are connected to the modular hub.

In various embodiments, the present method involves applying one or more of the pneumatically-actuated, modular components to the subject, wherein the pneumatically-actuated soft robotic gripper component is applied directly to a wound and/or the pneumatically-actuated tourniquet component is applied proximal to the wound, connecting the pneumatically-actuated, modular component to the modular hub and establishing a pneumatic connection between the gas supply and the component and a signal connection between the component and the controller, and pneumatically actuating the connected pneumatically-actuated, modular component with gas supplied from the gas supply such that the gripper component actuates to apply an effective amount of direct pressure to the wound to slow bleeding and/or the tourniquet component applies an effective amount of direct pressure proximal to the wound to stop or limit the blood flow to the wound.

In embodiments, the method further includes measuring the pressure applied by the pneumatically-actuated soft robotic gripper component and/or the pneumatically-actuated tourniquet component, and maintaining the pressure at, or adjusting the pressure to, a determined pressure level. In embodiments, the determined pressure level for the tourniquet component is ninety to one hundred mmHg above the systolic blood pressure of the subject. In other embodiments, the determined pressure level for the pneumatically-actuated tourniquet component is about forty mmHg greater than the limb occlusion pressure (LOP). In embodiments, the determined pressure level for the pneumatically-actuated gripper component is about one hundred seventy to one hundred ninety mmHg.

According to various embodiments of the present method, the gas supply is an air compressor, a gas storage tank for pressurized air, a pressurized gas canister, or any combination thereof.

According to various embodiments of the present method, the pneumatically-actuated, modular component is applied to a limb.

According to various embodiments of the present method, after pneumatically actuating the pneumatically-actuated, modular component connected to the modular hub with gas from the gas supply, the modular component is then disconnected from the modular hub, and the disconnected modular component continues to retain the gas and maintain the effective amount of pressure while disconnected.

In some embodiments, the wound is wrapped with gauze before applying the soft robotic gripper component to the wound.

According to various embodiments, the pneumatically-actuated soft robotic gripper component further includes a cooling unit or member positioned to be in contact with the subject in the area surrounding the wound when the soft robotic gripper component is actuated, and the present method includes cooling the area with the cooling unit. In some embodiments, the cooling unit is an ice pack or a cold pack, which is well-known and needs no further description or illustration. The cooling unit is typically disposed along the interior of the gripper pad 400 but may also be disposed along the exterior of the gripper pad 400.

Although various illustrative embodiments are described above, any of a number of changes may be made to various embodiments without departing from the scope of the invention as described by the claims. Optional features of various device and system embodiments may be included in some embodiments and not in others. Further, the particular features, structures or characteristics may be combined in any suitable manner in one or more embodiments. Therefore, the foregoing description is provided primarily for exemplary purposes and should not be interpreted to limit the scope of the invention as it is set forth in the claims.

What is claimed is:
1. A modular wound treatment system, comprising:
one or more pneumatically actuated modular components;
a modular hub having a modular connection for the one or more pneumatically actuated modular components which are selected from
    a pneumatically actuated soft robotic gripper component comprising a pneumatic network of channels and chambers (PneuNets) configured to curve and at least partially encircle a wound when pneumatically actuated and thereby apply direct pressure to the wound, and
    a pneumatically actuated tourniquet component configured to apply pressure proximal to the wound sufficient to limit blood flow to the wound;
a gas supply in pneumatic communication with the modular connection;
one or more sensors for measuring an amount of pressure being applied by the one or more pneumatically actuated modular components;
a controller for controlling the system; and
a display for providing system information to a user in signal communication with the controller,
the one or more pneumatically actuated modular components being in pneumatic communication with the gas supply, and being in signal communication with the controller, when the one or more pneumatically actuated modular components are connected to the modular hub,
the gas supply being configured to supply a gas to actuate the one or more modular components when the one or more modular components are connected to the modular hub,
the one or more modular components being configured to retain the gas supplied to them by the gas supply when the one or more modular components are disconnected from the modular hub,
the modular connection comprising a quick connect component that retains the pneumatic communication between the one or more modular components and the gas supply, and the signal communication between the one or more modular components and the controller, the quick connect component comprising:
    a valve for the pneumatic communication, the valve opening and establishing a pneumatic connection when the modular component is connected to the modular hub,
    an electrical connection for the signal communication, the electrical connection establishing the signal connection when the modular component is connected to the modular hub, and one or more pairs of magnets that establish a magnetic connection to hold the valve and the electrical connection in place when connected.

2. The modular wound treatment system of claim 1, wherein the modular hub actively is configured to regulate an amount of pressure applied by the one or more pneumatically actuated modular components.

3. The modular wound treatment system of claim 1, wherein the system information provided by the display is one or more of: an amount of pressure applied by the one or more pneumatically actuated modular components, an elapsed time that the one or more pneumatically actuated modular components have applied pressure to a subject, and a temperature of the subject in an area around the wound.

4. The modular wound treatment system of claim 1, further comprising a gas pressure regulator in fluid communication between the gas supply and the modular connection, the gas pressure regulator configured to provide a determined amount of gas to the one or more pneumatically actuated modular components.

5. The modular wound treatment system of claim 1, wherein the one or more pneumatically actuated modular components further comprise a temperature sensor in signal communication with the controller and positioned to be in contact with a subject in an area on or around the wound when the one or more modular components are actuated.

6. The modular wound treatment system of claim 5, wherein the temperature sensor comprises a thermocouple.

7. The modular wound treatment system of claim 1, wherein the gas supply comprises at least one of an air compressor, a gas storage tank for pressurized air, and a pressurized gas canister.

8. The modular wound treatment system of claim 1, wherein the controller distinguishes between the one or more modular components and determines which modular component is connected to the modular hub.

9. The modular wound treatment system of claim 1, wherein the signal communication comprises an inter-integrated circuit that allows the controller to identify the modular component connected to the modular hub.

10. The modular wound treatment system of claim 1, wherein the modular hub has a modular connection for at least two pneumatically actuated modular components, wherein the at least two pneumatically actuated modular components can be simultaneously connected to the hub.

11. The modular wound treatment system of claim 1, further comprising an alarm system that signals when one or more of: an amount of pressure applied by the one or more pneumatically actuated modular components are lower or higher than a determined level, an elapsed time that the one or more pneumatically actuated modular components have applied pressure exceeds a determined amount, and a gas supply is lower than a determined level.

12. The modular wound treatment system of claim 1, wherein the pneumatically actuated soft robotic gripper component comprises:
a network of inner cavities and channels (Pneu-nets) running through that allow and restrict gas flow to chosen parts of the soft robotic gripper component; and
a gas inlet port,
wherein activating the Pneu-nets causes the soft robotic gripper component to bend and curve in a predetermined manner to encircle a subject's limb and apply direct pressure to the limb.

13. The modular wound treatment system of claim 1, wherein the pneumatically actuated soft robotic gripper component comprises thermoplastic polyurethane (TPU).

14. The modular wound treatment system of claim 1, further comprising a base unit housing holding the gas supply, controller, and display.

15. The modular wound treatment system of claim 1, wherein the pneumatically actuated soft robotic gripper component further comprises a cooling unit positioned to be in contact with a subject in an area around the wound when the soft robotic gripper component is actuated.

16. The modular wound treatment system of claim 15, wherein the cooling unit comprises an ice pack.

17. A method of treating a subject having a wound, comprising:
providing a modular wound treatment system comprising:
a modular hub having a modular connection for one or more pneumatically actuated modular components;
the one or more components being one or more of:
a pneumatically actuated soft robotic gripper component comprising a pneumatic network of channels and chambers (PneuNets), the soft robotic gripper component configured to curve and at least partially encircle the wound when pneumatically actuated and thereby apply direct pressure to the wound, and
a pneumatically actuated tourniquet component configured to apply pressure proximal to the wound sufficient to limit blood flow to the wound;
a gas supply in pneumatic communication with the modular connection;
one or more sensors for measuring the pressure applied by the one or more pneumatically actuated modular components;
a display designed to provide system information to a user; and
a controller for controlling the system,
the one or more modular components being in pneumatic communication with the gas supply, and are in signal communication with the controller, when the one or more modular components are connected to the modular hub,
the gas supply supplying a gas to actuate the one or more modular components when the one or more modular components are connected to the modular hub,
the one or more modular components retaining the gas supplied to them by the gas supply when the one or more modular components are disconnected from the modular hub,
applying one or more of the pneumatically actuated modular components to the subject, the pneumatically actuated soft robotic gripper component being applied directly on the wound and/or the pneumatically actuated tourniquet component being applied proximal to the wound;
connecting said one or more pneumatically actuated modular components to the modular hub, and establishing a pneumatic connection between the gas supply and the one or more modular components and a signal connection between the one or more modular components and the controller;
pneumatically actuating the connected one or more pneumatically actuated modular components with gas supplied from the gas supply such that the soft robotic gripper component actuates to apply an effective amount of direct pressure to the wound to slow bleeding and/or the tourniquet component applies an effective amount of pressure proximal to the wound to stop or substantially limit the blood flow to the wound; and after pneumatically actuating the one or more pneumatically actuated modular components connected to the modular hub with gas from the gas supply, disconnecting the one or more pneumatically actuated modular components from the modular hub, the disconnected one or more pneumatically actuated modular components continuing to retain the gas and maintain the effective amount of pressure.

18. The method of claim 17, further comprising measuring the pressure applied by the pneumatically actuated soft robotic gripper component and/or the pneumatically actuated tourniquet component, and maintaining the pressure at, or adjusting the pressure to, a determined pressure level.

19. The method of claim 18, wherein the determined pressure level for the pneumatically actuated tourniquet component is about 90 to 100 mmHg above a systolic blood pressure of the subject.

20. The method of claim 18, wherein the determined pressure level for the pneumatically actuated tourniquet component is about 40 mmHg greater than a limb occlusion pressure (LOP).

21. The method of claim 18, wherein the determined pressure level for the pneumatically actuated soft robotic gripper component is about 170-190 mmHg.

22. The method of claim 17, wherein the gas supply is at least one of an air compressor and a pressurized gas canister.

23. The method of claim 17, wherein the one or more pneumatically actuated modular components are applied to a limb.

24. The method of claim 17, wherein the wound is wrapped with gauze before applying the soft robotic gripper component to the wound.

25. The method of claim 17, wherein the pneumatically actuated soft robotic gripper component further comprises a cooling unit positioned to be in contact with the subject in an area surrounding the wound when the soft robotic gripper component is actuated, and wherein the method further comprises cooling the area with the cooling unit.

26. A method of treating a subject having a wound, comprising:
   providing a modular wound treatment system comprising:
      a modular hub having a modular connection for one or more pneumatically actuated modular components; the one or more components being one or more of:
      a pneumatically actuated soft robotic gripper component comprising a pneumatic network of channels and chambers (PneuNets), the soft robotic gripper component configured to curve and at least partially encircle the wound when pneumatically actuated and thereby apply direct pressure to the wound, and
      a pneumatically actuated tourniquet component configured to apply pressure proximal to the wound sufficient to limit blood flow to the wound;
      a gas supply in pneumatic communication with the modular connection;
      one or more sensors for measuring the pressure applied by the one or more pneumatically actuated modular components;
      a display designed to provide system information to a user; and
      a controller for controlling the system,
      the one or more modular components being in pneumatic communication with the gas supply, and are in signal communication with the controller, when the one or more modular components are connected to the modular hub,
      the gas supply supplying a gas to actuate the one or more modular components when the one or more modular components are connected to the modular hub,
      the one or more modular components retaining the gas supplied to them by the gas supply when the one or more modular components are disconnected from the modular hub,
   applying one or more of the pneumatically actuated modular components to the subject, the pneumatically actuated soft robotic gripper component being applied directly on the wound and/or the pneumatically actuated tourniquet component being applied proximal to the wound;
   connecting said one or more pneumatically actuated modular components to the modular hub, and establishing a pneumatic connection between the gas supply and the one or more modular components and a signal connection between the one or more modular components and the controller; and
   pneumatically actuating the connected one or more pneumatically actuated modular components with gas supplied from the gas supply such that the soft robotic gripper component actuates to apply an effective amount of direct pressure to the wound to slow bleeding and/or the tourniquet component applies an effective amount of direct pressure proximal to the wound to stop or substantially limit the blood flow to the wound,
   the one or more pneumatically actuated modular components being connected to the modular hub via the modular connection which comprises a quick connect component that retains the pneumatic communication between the one or more modular components and the gas supply, and the signal communication between the one or more modular components and the controller, the quick connect component comprising:
      a valve for the pneumatic communication, the valve opening and establishing a pneumatic connection when the modular component is connected to the modular hub,
      an electrical connection for the signal communication, the electrical connection establishing the signal connection when the modular component is connected to the modular hub, and one or more pairs of magnets that establish a magnetic connection to hold the valve and the electrical connection in place when connected.

27. The method of claim 26, further comprising measuring the pressure applied by the pneumatically actuated soft robotic gripper component and/or the pneumatically actuated tourniquet component, and maintaining the pressure at, or adjusting the pressure to, a determined pressure level.

28. The method of claim 26, further comprising, after pneumatically actuating the one or more pneumatically actuated modular components connected to the modular hub with gas from the gas supply, disconnecting the one or more pneumatically actuated modular components from the modular hub, the disconnected one or more pneumatically actuated modular components continuing to retain the gas and maintain the effective amount of pressure.

* * * * *